United States Patent
Harrell et al.

[11] Patent Number: 5,876,678
[45] Date of Patent: Mar. 2, 1999

[54] TEAM SPIRIT AIR FRESHENER

[76] Inventors: Stacy Harrell, 10314 Zachary Cir., #118; Steve Romanoli, 10310 Zachary Cir., #69, both of Riverview, Fla. 33569

[21] Appl. No.: 916,645

[22] Filed: Aug. 22, 1997

[51] Int. Cl.⁶ .................................................. A61L 9/00
[52] U.S. Cl. .............................. 422/125; 422/5; 422/123; 422/306; 422/307; 392/390; 392/393; 239/53; 239/55; D23/366; D23/368
[58] Field of Search ...................... 422/4, 5, 120, 422/123, 124, 125, 306, 307; 392/387, 390, 393; 239/53–55; D23/366–368; 222/187

[56] References Cited

U.S. PATENT DOCUMENTS

| | | | |
|---|---|---|---|
| D. 275,786 | 10/1984 | Reedman | D23/368 |
| 3,220,913 | 11/1965 | Thomas | 222/187 |
| 3,924,807 | 12/1975 | Morgan | 239/55 |
| 3,948,445 | 4/1976 | Andeweg | 422/125 |
| 4,219,531 | 8/1980 | Wisnieski | 422/124 |
| 4,285,905 | 8/1981 | Feit | 422/4 |
| 4,306,892 | 12/1981 | Atulla et al. | 55/279 |
| 4,346,059 | 8/1982 | Spector | 422/4 |
| 4,708,851 | 11/1987 | Loringhoven | 422/123 |
| 4,714,984 | 12/1987 | Spector | 422/5 |
| 4,919,925 | 4/1990 | Ueda et al. | 422/5 |
| 4,995,556 | 2/1991 | Arnold, III | 239/57 |
| 5,240,653 | 8/1993 | Ramkissoon | D23/366 |

*Primary Examiner*—Krisanne Thornton
*Assistant Examiner*—Fariborz Moazzam
*Attorney, Agent, or Firm*—Joseph N. Breaux

[57] ABSTRACT

An air freshener which has a rigid plastic frame, a hollow shell of translucent, open cell foam which is placed over the frame and which is impregnated with a scent agent, a base which is removably connected to the frame and which has a light bulb extending therefrom into the interior of the frame for illuminating the shell and for heating the scent agent to increase its dispersion. The frame and shell are manufactured in the shape of a basketball, baseball, or other piece of sports equipment and the shell is imprinted with a name or team logo.

4 Claims, 2 Drawing Sheets

TEAM SPIRIT AIR FRESHENER

TECHNICAL FIELD

The present invention relates to air fresheners and more particularly to an automobile air freshener which has the shape of sports equipment such as a basketball or a baseball glove and which has a small bulb therein for illuminating the air freshener and a team logo thereon and also for enhancing the effectiveness of the freshening agent by providing warmth to increase the activity of the agent.

BACKGROUND OF THE INVENTION

Because the interiors of automobiles are usually completely closed, either to prevent the passengers' exposure to the weather or to protect the contents of the vehicle, they can become stuffy, stale and uncomfortable environments. Air fresheners are therefore widely used to scent the air and provide a more pleasant conditions for persons riding in the automobile. Air fresheners found in the prior art include several different types, including scented liquids which are sprayed into the air or onto the carpet, and solid fresheners which are placed under the seats, on the dashboard or on strings which allow the air freshener to be hung from the rear view mirror.

The solid air fresheners are manufactured in a number of shapes. The under-seat type of air freshener need not be attractively packaged since it is to be placed out of sight and it may have a simple cylindrical or box-shaped container. The hanging type, on the other hand, is intended to be placed in a much more visible location and attempts are therefore made to make the air freshener more attractive, or at least to minimize its unattractiveness. This is usually accomplished by manufacturing this type of air freshener in a flat, card-like shape which can be printed on its two sides or which can be cut into a silhouette, such as that of a pine tree. Because these card-like air fresheners are typically just pieces of porous cardboard-like material, they do not last as long as the under-seat type.

SUMMARY OF THE INVENTION

It is thus an object of the invention to provide an air freshener than can be hung from a rear view mirror or other protruding object.

It is a further object of the invention to provide an air freshener that has a three-dimensional shape resembling sports equipment.

It is a still further object of the invention to provide an air freshener that is manufactured in a form which is suitable for displaying.

It is a still further object of the invention to provide an air freshener that provides an illuminated package for displaying a name or team logo.

It is a still further object of the invention to provide an air freshener that has a warming element for enhancing the scent-producing capacity of the air freshener.

Accordingly, an air freshener which has a rigid elastic frame, a hollow shell of translucent, open cell foam which is placed over the frame and which is impregnated with a scent agent, a base which is removably connected to the frame and which has a light bulb extending therefrom into the interior of the frame for illuminating the shell and for heating the scent agent to increase its dispersion is provided. The frame and shell are manufactured in the shape of a basketball, baseball or other piece of sports equipment and the shell is imprinted with a name or team logo so that the logo can be displayed by hanging the air freshener from a rear view mirror or by placing the air freshener on a flat surface such as a dashboard, desk or shelf.

BRIEF DESCRIPTION OF DRAWINGS

For a further understanding of the nature and objects of the present invention, reference should be had to the following detailed description, taken in conjunction with the accompanying drawings, in which like elements are given the same or analogous reference numbers and wherein.

DESCRIPTION OF THE EXEMPLARY EMBODIMENT

Figure 1:
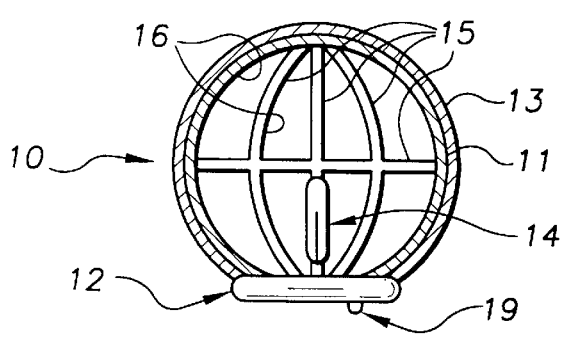
FIG. 1 is a cut away plan view of the body of the invention.
Figure 2:
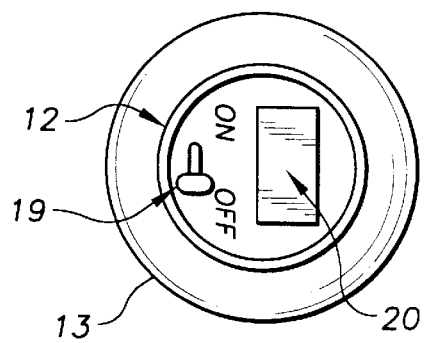
FIG. 2 is a plan view of the bottom of the invention.

Referring to FIG. 1, the internal structure of the ball assembly of the invention, generally designated by the numeral 10, is shown. The ball assembly comprises a frame 11 with a base 12, an cuter shell 13 and a light bulb 14. Frame 11 is generally spherical and has a number of ribs 15 which have openings 16 therebetween. Shell 13 covers the exterior of frame 11 and encloses the space defined by the frame except for an opening at the bottom of the frame. The material of shell 13 is translucent. Base 12 is connected to the bottom of frame 11 and is removable to allow access to the interior of the frame.

Base 12 is in the shape of a disk and has a light bulb 14 which extends outward from the center of one of the flat sides of the base. Base 12 is attachable to frame 11 so that light bulb 14 extends into the interior of frame 11. Base 12 has a battery compartment 17 therein for holding a battery 18 to provide power for light bulb 14. On the side of base 12 opposite light bulb 14 is on/off switch 19. Battery compartment door 20 encloses battery compartment 17.

Figure 3:
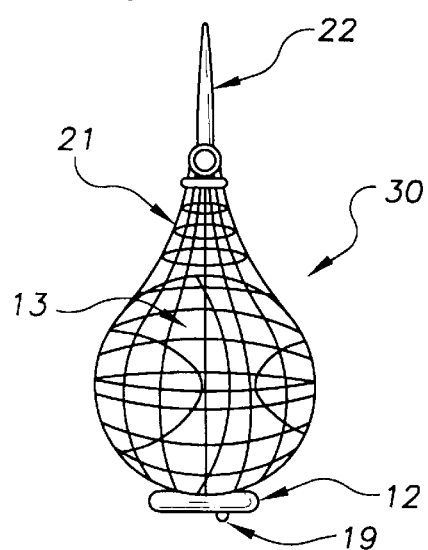
FIG. 3 is a perspective view of a basketball embodiment of the invention.

Referring to FIG. 3, the exterior of invention 30 is shown. Shell 13 is patterned to resemble a basketball. The shell can easily be imprinted with the logo of a team so that the shell and logo can be displayed, either with or without illumination from light bulb 14 within ball assembly 10. Ball assembly 10 is enclosed within net 21, which has a filament 22 at its upper end for hanging the invention on a rear view mirror or other object. The filament 22 is attached to net 21 by a small closure which holds the upper edge of net 21 together at a single point and which has a loop through which filament 22 can be threaded and thereby attached. Net 21 has a small opening at its lower end through which base 12 can extend slightly so that the base can be removed from frame 11 without removing the ball assembly 10 from net 21.

Frame 11 is manufactured from a plastic such as ABS plastic using an injection molding process. Shell 13 is manufactured from open-cell foam board and is cut into appropriate shapes using steel ruled dies. The foam board pieces of shell 13 are preferably printed with the appropriate design before assembly with the frame. The printing is accomplished by using a silkscreen printing process. The printing of the shell may include the printing of a logo, or the logo may be manufactured as an applique which is later applied to the shell.

The open-cell structure of the foam board allows this material to absorb moisture and/or liquids so that the shell can be impregnated with a scented liquid to provide air freshening capability. The foam board shell is impregnated during manufacturing with a liquid which is a carrier for a volatile scent agent. "Volatile" here is used to describe the tendency of the scent agent to disperse itself into its surroundings, whether at a slow or fast rate. The foam board may also be considered a carrier for the liquid. As a part of the manufacturing process, the liquid is allowed to evaporate, leaving the scent agent in the open cells of the foam board where they can slowly disperse into the air around the air freshener. The scented liquid could be reapplied by the user after several months of use.

The net around the air freshener is made from a nylon mesh or similar material. The filament can be made of the same material as the net, in which case the length of the filament is preferably adjustable, or it can be made from a loop of elastic material which has a length appropriate to allow the filament to be stretched over a rear view mirror or other objects from which the invention is hung.

Figure 5:
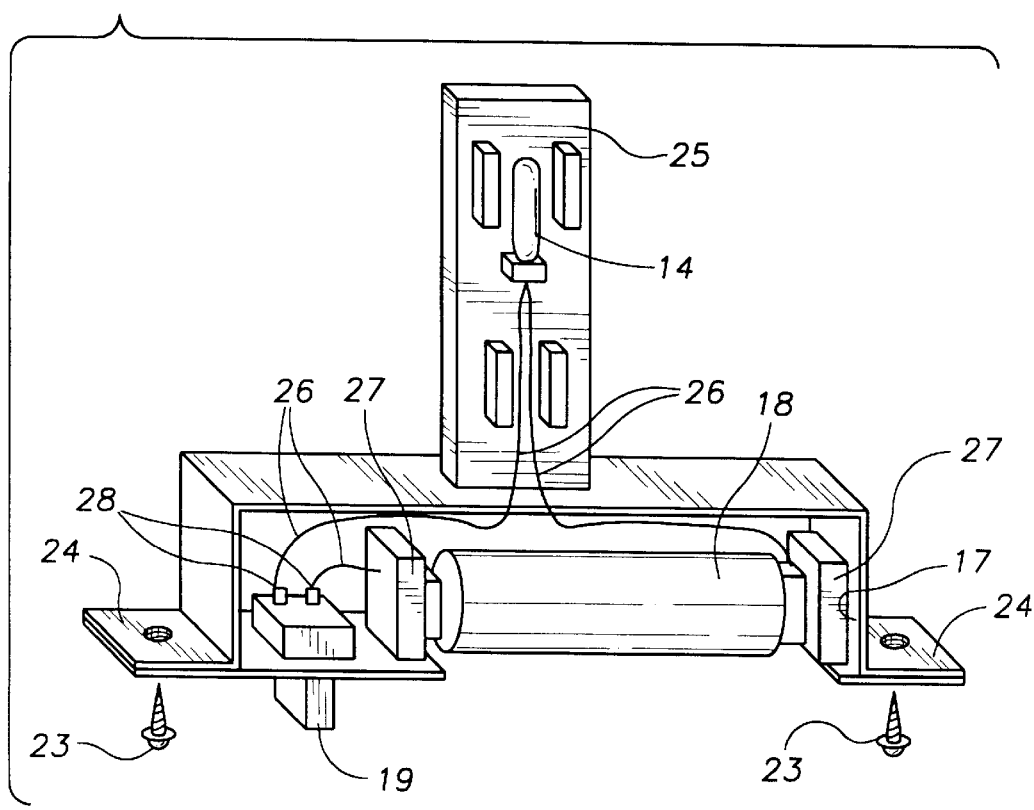
FIG. 5 is a cut away perspective view of the battery compartment and light bulb assembly of the invention.
Figure 6:
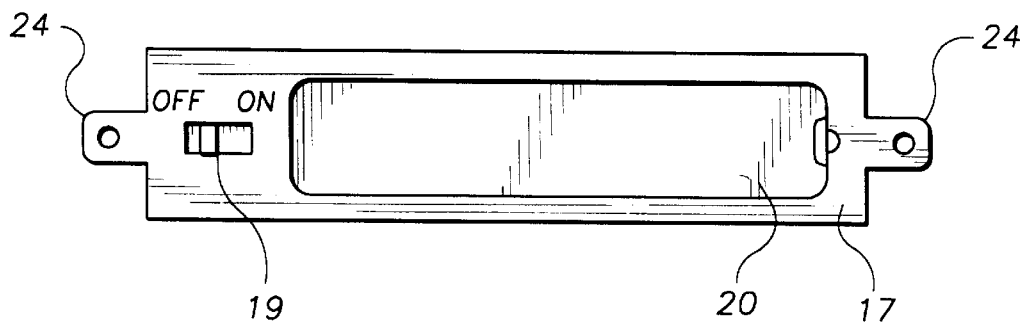
FIG. 6 is a plan view of the battery compartment and light bulb assembly of the invention.

The base and battery compartment components of the invention can be manufactured using the injection molding process, but are readily available as remanufactured components. Base 12 need not be removable if the lightbulb 14 and/or battery compartment 17 are removable apart from the base. FIG. 5 shows a premanufactured battery compartment/lightbulb assembly which is inserted into base 12. The assembly has tabs 24 at each end and is held in place by means of two sheet metal type screws 23 which are placed through the tabs and screwed into the base. The battery is enclosed within the battery compartment by compartment door 20 as shown in FIG. 6.

The assembly of FIG. 5 has a light bulb bracket 25 attached to the side of battery compartment 17 and extending away therefrom. The light bulb 14 has a wattage similar to that of a standard Christmas tree bulb. A pair of wires 26 connect the electrodes of light bulb 14 to one of the battery contacts 27 and one of the switch contacts 28. Another wire 26 connects the remaining contacts of the battery and switch to complete the circuit. It is also envisioned that simple insertion and removal of the battery could serve as the switch mechanism.

Figure 4:
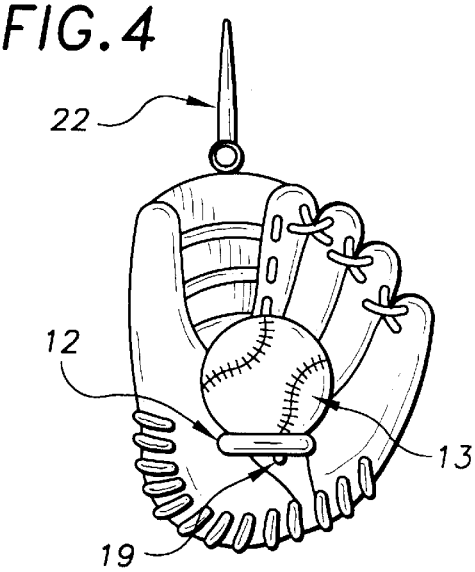
FIG. 4 is a perspective view of a baseball/glove embodiment of the invention.

The invention may be modified in many ways from the embodiment described above. Modifications may be relatively minor, such as the use of a frame which has a loop directly attached to the top of the frame through which a string can be threaded to provide means for hanging the invention. Materials other than open cell foam board may also be used to form the shell if they provide suitable means to retain the air freshening scent. Other modifications may be more substantial. For example, the frame and shell may be manufactured as a single piece of injectable foam. The invention may also be manufactured in the shape of articles other than a basketball, such as the baseball and glove shown in FIG. 4. In such an embodiment, either the baseball or the glove or both can be manufactured as the air freshening frame/shell portion of the invention.

The invention is used by simply placing it in the location in which the air freshening is required. As mentioned above, the invention can be hung from a rear view mirror in an automobile and it can also be placed on the dashboard so that it sits on its base. The invention may likewise be hung or placed on its base in a room, such as a child's bedroom, on a shelf or in any other suitable location.

The invention may be used to display the logo of a favorite team or a child's name by imprinting the name or logo directly on the shell or by printing an applique which is then applied to the shell. The light bulb within the frame can be turned on to illuminate the logo for better viewing. The light bulb can also be turned on to provide a heat source to accelerate the rate at which the scent escapes from the shell and enters the environment around the invention. Thus, if more air freshening is required, the light bulb is simply turned on—the invention does not have to be moved or mechanically adjusted.

It can be seen from the preceding description that a device for freshening stale air which can be hung from a rear view mirror or other protruding object, has a three-dimensional shape resembling sports equipment, is manufactured in a form which is suitable for displaying, provides an illuminated package for displaying a name or team logo and has a warming element for enhancing the scent-producing capacity of the air freshener has been provided.

It is noted that the embodiment of the air freshener described herein in detail for exemplary purposes is of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. An air freshener comprising:

a body having a scented portion, said body being translucent and having a cavity therein for receiving a light bulb, said body including a molded plastic frame constructed from a number of spaced plastic ribs having openings therebetween and defining said cavity therein, and an outer shell constructed from a translucent open celled foam having a printable exterior surface, said outer shell covering the frame and enclosing said space defined by said frame except for a bottom opening through a bottom portion of said frame, said outer shell being impregnated with a volatile scent agent that disperses at a rate which is sensitive to heat;

a light bulb disposed within said cavity through said bottom opening for illuminating said body, said light bulb having a power switch with an on position in which said light bulb is illuminated and an off position in which said light bulb is not illuminated, said rate being at a first level when said light bulb is not illuminated, said rate being at a second level higher than said first level when said light bulb is illuminated.

2. The air freshener of claim 1, further comprising a net enclosure, said body being disposed within said net enclosure, said net enclosure having a loop at an upper end thereof for hanging said net enclosure from an object.

3. The air freshener of claim 2, further comprising a base connected to a lower end of said body, said base being shaped to hold said body upright when said base is placed on a flat surface, said base having a battery compartment and a battery disposed within said battery compartment, said battery being electrically connected to said light bulb to provide power thereto, said light bulb being connected to said base, said base and said light bulb being removable from said body.

4. The air freshener of claim 3 wherein said scented portion of said body comprises a carrier which is impregnated with a scent agent, said scent agent being volatile and dispersing at a rate which is sensitive to heat, said rate being at a low level when said light bulb is not illuminated, said rate being at a high level when said light bulb is illuminated.

* * * * *